Figure 1:
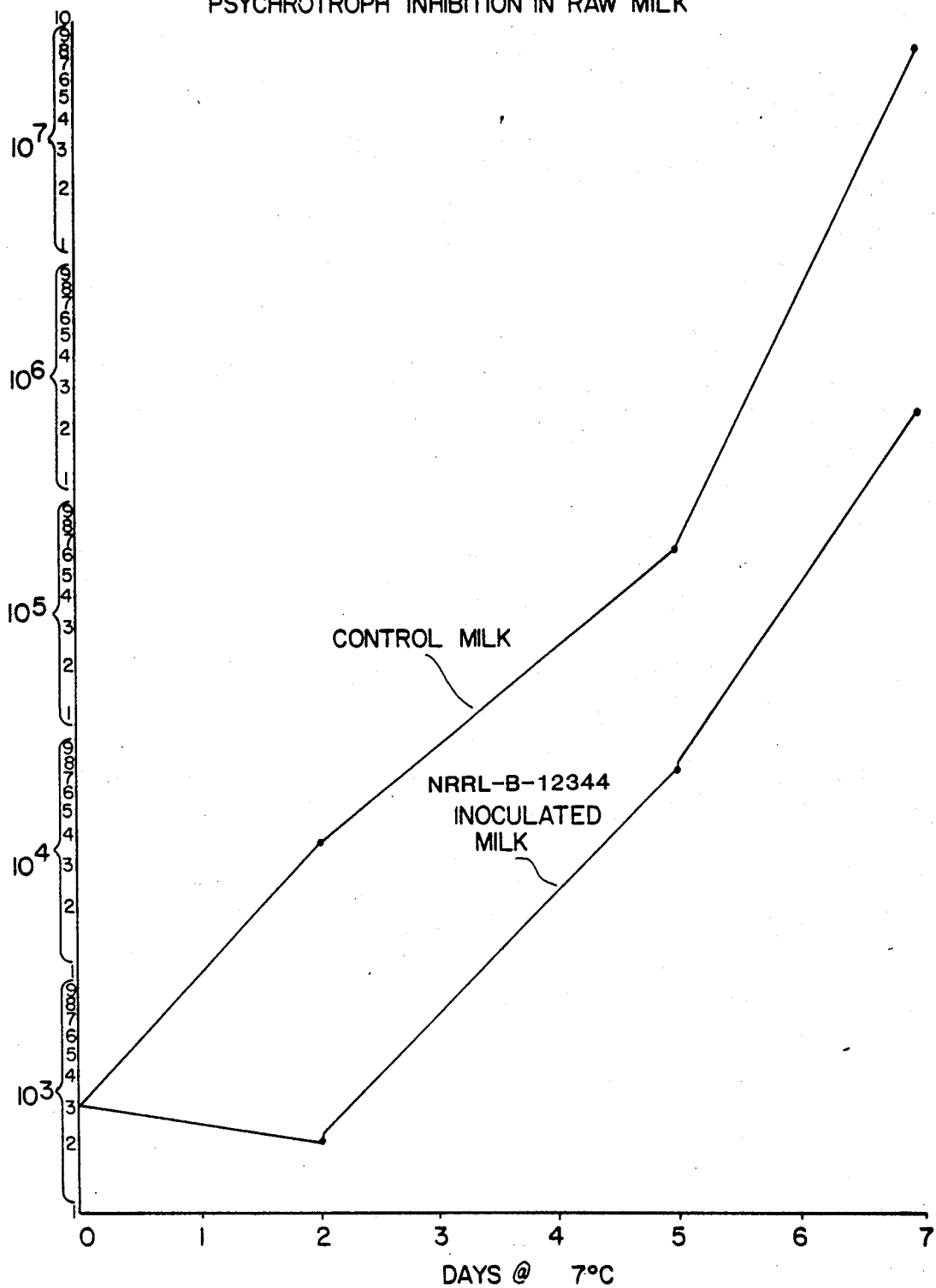

United States Patent [19]

Matrozza et al.

[11] Patent Number: 4,912,047
[45] Date of Patent: Mar. 27, 1990

[54] PREVENTING PSYCHROTROPHIC BACTERIAL SPOILAGE IN RAW MILK

[75] Inventors: Mark A. Matrozza, Sarasota; Marianne F. Leverone, Bradenton; Donald P. Boudreaux, Sarasota, all of Fla.

[73] Assignee: Microlife Technics, Inc., Sarasota, Fla.

[21] Appl. No.: 49,852

[22] Filed: May 15, 1987

[51] Int. Cl.$^4$ .................. C12R 1/01; C12R 1/245; A23C 3/00
[52] U.S. Cl. .................. 435/252.9; 426/61; 426/330.2; 435/856
[58] Field of Search ............... 435/252.9, 856; 426/61, 426/330.2

[56] References Cited

U.S. PATENT DOCUMENTS

| 4,320,116 | 3/1982 | Björck | 424/129 |
| 4,477,471 | 10/1984 | Gonzalez | 435/172.3 |
| 4,514,424 | 4/1985 | Raccach | 426/56 |

FOREIGN PATENT DOCUMENTS 1087019 10/1980 Canada ........................ 426/330.2

OTHER PUBLICATIONS

Sneath et al., *Bergey's Manual of Systematic Bacteriology*, vol. 2, 1986, p. 1226.
Gilliland et al., J. Dairy Sci. 66: 974–980 (1983).
Björck et al., Applied Microbiology 30: 199–204 (1975).
Reiter et al., J. of Food Protection, 47: 724–732 (1984).
Thomas et al., Infection and Immunity 20: 456–463 (1978).
Northolt, Neth. Milk Dairy J. 38: 135–150 (1984).
Sellars et al., 7th Biennial Cheese Conference, Aug. 26–28, 1986 at Utah State University.
Gilliland et al., Am. Public Health Assoc., M. L. Speck, ed. 173–178 (1976).

*Primary Examiner*—Robert A. Wax
*Attorney, Agent, or Firm*—Ian C. McLeod

[57] ABSTRACT

An improved method for inhibiting psychrotrophic bacteria in raw milk is described. The method uses a non-lactose fermenting strain of a lactobacillus to generate hydrogen peroxide which inhibits the psychrotrophic bacteria. A preferred strain is *Lactobacillus casei* subspecies alactosus NRRL-B-12344 which is a superior producer of hydrogen peroxide at 5° to 8° C.

6 Claims, 1 Drawing Sheet

PREVENTING PSYCHROTROPHIC BACTERIAL SPOILAGE IN RAW MILK

BACKGROUND OF THE INVENTION

(1) Field of the Invention

The present invention relates to an improved method for inhibiting psychrotrophic bacteria in raw milk. In particular the present invention relates to a method wherein a non-lactose fermenting lactobacillus which produces hydrogen peroxide at refrigeration temperatures is added to the milk.

(2) Prior Art

Gilliland et al, J. Dairy Sci. 66, 974–980 (1983) described the use of various strains of lactose fermenting lactobacilli which generate hydrogen peroxide and activates a thiocyanate lactoperoxidase system in raw milk to inhibit psychrotrophic bacteria at 5° C. or 7° C. either alone or with a sorbate. Four (4) day cell counts of non-lactobacilli (i.e. psychrotrophic bacteria) were reduced by the use of the lactobacilli, particularly in the presence of sorbate. Other related references are L. Bjorck et al, Applied Microbiology 30, 199–204 (1975); B. Reiter et al., J. of Food Protection, 47, 724–732 (1984); E. L. Thomas et al., Infection and Immunity, 20, 456–463 (1978); and M. D. Northolt, Neth. Milk Dairy J. 38, 135–150 (1984).

Cultures are sold commercially for use in raw milk for cheese making as described in a paper by Sellars, R. L. et al at the 7th Biennial Cheese Conference, held Aug. 26–28, 1986 at Utah State University. The problem is that there is a need for cultures for use in raw milk which may be exposed to higher temperatures in transit without generating lactic acid from lactose in the milk. It is also important to generate significant amounts of hydrogen peroxide at refrigeration temperatures in the milk.

U.S. Pat. No. 4,320,116 to Bjorck et al. describes the use of chemical additives in milk including lactoperoxidase, a peroxide salt and a thiocyanate salt. The problem is that the raw milk is considered to be legally adulterated for some applications such as bottled milk.

The prior art has needed a reliable non-chemical method of preserving raw milk. The bacterial methods of the prior art have not satisfied this need because of lactose fermentation by the lactobacillus and/or insufficient hydrogen peroxide production at refrigeration temperatures.

OBJECTS

It is therefore an object of the present invention to provide a method wherein raw milk is preserved using selected naturally occurring strains of Lactobacillus which do not acidify the milk because they are not lactose fermenting. Further it is an object of the present invention to provide strains of Lactobacillus which generate significant amounts of hydrogen peroxide at low temperatures (5° to 8° C.). Further still it is an object of the present invention to provide a method which is simple and economical. These and other objects will become increasingly apparent by reference to the following description and the drawing.

IN THE DRAWING

FIG. 1 is a graph showing the inhibition of psychrotrophic bacteria in raw milk using a preferred strain Lactobacillus casei subspecies alactosus NRRL-B-12344 which is lactose negative.

GENERAL DESCRIPTION

The present invention relates to an improved method of inhibiting spoilage by psychrotrophic bacteria in raw milk by introducing a Lactobacillus into the milk which comprises providing a Lactobacillus which does not ferment lactose in the milk, wherein the Lactobacillus produces hydrogen peroxide which initiates inhibition of the psychrotrophic bacteria in the milk. The lactose negative Lactobacillus do not generate lactic acid even if the milk is allowed to warm because of poor refrigeration which is a problem.

The inhibition of the psychrotrophic bacteria results from hydrogen peroxide production by the Lactobacillus which activates the thiocyanate lactoperoxidase system of the raw milk. The hydrogen peroxide reacts with thiocyanate in the milk to produce a thiocyanate ion. Lactoperoxidase in the raw milk catalyzes the incorporation of the thiocyanate ion into the psychrotrophic bacteria to cause the inhibition. The exact mechanism of inhibition is unknown. The method has the advantage of not requiring the addition of chemicals to the milk which can be regarded as causing adulteration.

U.S. Pat. No. 4,514,424 to Raccach describes the preferred strain Lactobacillus casei subspecies alactosus NRRL-B-12344 of the present invention. The methods of preserving this strain and related strains which do not ferment lactose are described in this patent. The prior art has not recognized that the preferred lactose negative strain Lactobacill-us casei subspecies alactosus is a significant producer of hydrogen peroxide. In meat fermentations this is a disadvantage, causing what is known as the "green ring" defect. This strain has not been used commercially in meat fermentations for this reason. The present invention was the first to recognize this strain could be used in preserving raw milk. The preferred strain has the advantage that it is active in generating hydrogen peroxide at low temperatures (5° C. to 8° C.). Other lactose negative strains can easily be isolated from naturally occurring strains or produced by mutation of lactose fermenting strains using mutagenic agents.

Generally the bacterial concentrates contain between about $1 \times 10^7$ and $1 \times 10^{13}$ cells per gram, usually between $1 \times 10^9$ and $1 \times 10^{12}$ cells per gram. The cells can be frozen or lyophilized and usually have a pH between about 4 and 8. All of this technology relating to preserving bacteria is well known to those skilled in the art.

SPECIFIC DESCRIPTION

EXAMPLE 1

Hydrogen peroxide production by Lactobacillus casei subspecies alactosus (NRRL-B-12344).

Lactic acid bacteria were compared for their hydrogen peroxide producing ability. All except Lactobacillus casei subspecies alactosus produce lactic acid from lactose. The test strains were grown in MRS broth (Difco) at 32° C. for about 20 hours. The cells were harvested by centrifugation. The cells were resuspended in 30 ml of the supernatant and glycerine was added for a final concentration of 10% by volume. The stock strains were frozen at −20° C. and stored at this temperature until needed.

To assay for hydrogen peroxide production, the stock culture was diluted to a cell concentration of $1 \times 10^{10}$ CFU/ml in water. One microliter of this diluted culture ($1 \times 10^7$ CFU) was spotted on hydrogen peroxide indicator plates. The plates consisted of 8.5% non-fat dry milk and 1.5% agar. The medium was sterilized and cooled to 45° C. To the tempered medium, 0.67 ml of a filter sterilized peroxidase solution (Sigma Chemical Co. 40 U/ml) and 1.0 ml of a filter sterilized 0.274% solution of 2-2'-azinobis(3-ethylbenzothiozoline-6-sulfonic acid), diammonium salt (ABTS; Aldrich Chemical Co.) was added. Spotted plates were incubated at 23° C. and 8° C. for 18 hours. The presence of hydrogen peroxide was indicated by a blue zone the diameter of which was proportional to the amount of hydrogen peroxide produced.

As shown in Table 1, hydrogen peroxide production by test strains did not differ greatly at 23° C. but at 8° C. strain Lactobacillus casei subspecies alactosus (NRRL-B-12344) produced about twice the amount of hydrogen peroxide as the next best strain. This is especially significant since this invention uses hydrogen peroxide for the preservation of raw milk at refrigeration temperatures. Thus L. casei subspecies alactosus (NRRL-B-12344) is a much stronger producer of hydrogen peroxide under conditions of the intended use of this invention and does not produce lactic acid from lactose.

TABLE 1

Hydrogen Peroxide Production by Selected strains of lactic-acid bacteria at 23° C. and 8° C[1].

| Incubation Time (h) | Incubation Temp (°C.) | Zone diameter (mm) on lactoperoxidase agar assay plates for tested strains | | | | |
|---|---|---|---|---|---|---|
| | | 12344[2] | 5628[3] | 12315[4] | HL[5] | HS[6] |
| 15 | 23 | 9.5 | 9.0 | 8.0 | 0 | 3.0 |
| | 8 | 10.0 | 5.0 | 5.5 | 0 | 3.0 |
| 24 | 23 | 10 | 11 | 10.5 | 0 | 4.5 |
| | 8 | 11 | 6 | 5.5 | 0 | 4.5 |
| 48 | 23 | 10 | 12.5 | 12 | 0 | 4.5 |
| | 8 | 11 | 6 | 5.5 | 0 | 6.5 |
| 120 | 23 | 10 | 13 | 12.5 | 0 | 5.5 |
| | 8 | 11 | 7 | 5.5 | 0 | 11.7 |

[1] $1 \times 10^7$ cfu of test strain spotted on surface of Lactoperoxidase agar. Medium consisted of 8.5% NFDM + 1.5% agar. To the sterile medium was added 0.67 ml of a filter sterilized solution of peroxidase (40 U/ml) and 1.0 ml of a 0.274% filter sterilized solution of ABTS.
[2] 12344 = Lactobacillus casei subspecies alactosus (NRRL-B-12344).
[3] 5628 = Lactobacillus lactis (NRRL-B-5628). Farr strain reported by Gilliland and Ewell (1983) J. Dairy Sci. 66:974.
[4] 12315 = Lactobacillus lactis NRRL-B-12315. Strain reported by Gilliland and Ewell (1983) J. Dairy Sci. 66:974.
[5] HL = Lactobacillus sp. isolated from commercial raw milk inoculant.
[6] HS = Streptococcus sp. isolated from commercial raw milk inoculant.

EXAMPLE 2

Preservation of Raw Milk

Procedure—Raw milk was obtained from a local dairy. The milk was divided into 2 x 100 ml portions in sterile bottles. One bottle of the raw milk was inoculated with Lactobacillus casei subspecies alactosus NRRL-B-12344 at $4 \times 10^7$ cells/ml. The concentrate cell count was $79 \times 10^8$/ml. The other bottle served as a control. The 0 hr pH and psychrotroph count of the raw milk is shown in Table 2. The pH of both bottles was tested after 2 and 5 days incubation at 7° C. The psychrotroph count (CVT count) was conducted as described by Gilliland et al (psychrotrophic microorganisms in Compendium of Methods for the Microbiological Examination of Foods. American Public Health Association, Marvin L. Speck, ed. 173–178 (1976)) after 2, 5 and 7 days incubation at 7? C.

RESULTS

TABLE 2

| | | Raw | Inoc. Raw |
|---|---|---|---|
| 0 Hr | pH | 6.68 | 6.68 |
| | CVT[1] | $29 \times 10^2$ | $29 \times 10^2$ |
| 2 days | pH | 6.69 | 6.68 |
| | CVT | $36 \times 10^3$ | $20 \times 10^2$ |
| 5 days | pH | 6.61 | 6.53 |
| | CVT | $60 \times 10^4$ | $74 \times 10^3$ |
| 7 days | CVT | $72 \times 10^6$ | $74 \times 10^4$ |

[1] CVT = Psychrotroph Count.

As can be seen from Table 2, the Lactobacillus casei subspecies alactosus NRRL-B-12344 significantly inhibited psycrotrophic bacteria even at the relatively high levels of psychrotropic bacteria in the test milk. The results are plotted in FIG. 1.

EXAMPLE 3

Preservation of Raw Milk

Procedure—Raw milk was obtained from a local dairy. The milk was divided into $5 \times 100$ ml portions in sterile bottles. The bottles of raw milk were inoculated with Lactobacillus casei subspecies alactosus NRRL-B-12344 at rates between $1 \times 10^5$ cfu/ml and $1 \times 10^6$ cfu/ml. The concentrate cell count was $79 \times 10^8$/ml. One bottle was not inoculated as a control. The initial pH was 6.64.

The psychrotroph count (CVT count) was conducted as described by Gilliland et al. (Psychrotrophic Microorganisms in Compendium of Methods for the Microbiological Examination of Foods. American Public Health Association, Marvin L. Speck, ed. 173–178 (1976)) after 2, 3 and 6 days incubation at 7° C.

Inhibition of psychrotrophic bacteria was achieved at a Lactobacillus casei subspecies alactosus rate of $1 \times 10^6$ cfu/ml (Table 3). When the bacterial count was decreased to $5 \times 10^5$ cfu/ml some inhibition was observed for 3 days. No inhibition of psychrotrophic bacteria was obtained in raw milk inoculated with Lactobacillus casei subspecies alactosus at $1 \times 10^5$ cfu/ml.

TABLE 3

Inhibition of psychrotrophic bacteria in raw milk by Lactobacillus casei subspecies alactosus at 7° C.

| L. casei cfu/ml | Psychrotroph count (days at 7° C.) $\times 10^4$ | | | |
|---|---|---|---|---|
| | 0 | 2 | 3 | 6 |
| 0 | 0.69 | 2.74 | 6.60 | 1510 |
| $1 \times 10^5$ | | 1.87 | 6.80 | 2140 |
| $5 \times 10^5$ | | 1.76 | 3.60 | 3180 |
| $1 \times 10^6$ | | 1.20 | 1.60 | 350 |

Preferably between about $10^6$ and $10^8$ cells per ml of the Lactobacillus are provided in the milk. It is also preferred that the milk be refrigerated at between about 5° to 8° C. except for periods when the refrigeration is ineffective.

It is intended that the foregoing description be illustrative of the present invention and that the present invention be limited by the hereinafter appended claims.

I claim:

1. In a method of inhibiting spoilage by psychrotropic bacteria in raw milk by introducing a Lactobacilis into the milk the improvement which comprises providing cells of *Lactobacillus casei* subspecies alactosus NRRL-B-12344 in the milk, wherein the *Lactobacillus casei* produces hydrogen peroxide at a temperature between about 5 and 80° C. which initiates inhibition of the psychrotrophic bacteria in the milk does not ferment lactose in the milk.

2. The method of claim 1 wherein between about $10^6$ and $10^8$ cells per ml are provided in the milk.

3. The method of claim 1 wherein a zone of peroxide production at 8° C. is at least about 10 mm as measured by an assay using peroxidase and a chromogen in a non-fat dry milk containing agar with $10^7$ of the Lactobacillus spotted on the agar, wherein the chromogen is oxidized to produce a color by reaction of the peroxidase with the peroxide.

4. The method of claim 3 wherein the chromogen is 2-2, azinobis(3-ethylbenzothiozoline-6-sulfonic acid) diammonium salt which is oxidized to a purple color.

5. The method of claim 1 wherein the raw milk is refrigerated at the temperature between about 5 and 8° C. except for periods when the refrigeration is ineffective.

6. The method of claim 1 wherein between about $10^6$ and $10^8$ cells of the *Lactobacillus casei* per ml of milk are in the milk.

* * * * *

UNITED STATES PATENT AND TRADEMARK OFFICE
CERTIFICATE OF CORRECTION

PATENT NO. : 4,912,047

DATED : March 27, 1990

INVENTOR(S) : Mark A. Matrozza, et al

It is certified that error appears in the above-identified patent and that said Letters Patent is hereby corrected as shown below:

Column 2, line 34, "Lactobacill-us" should be --Lactobacillus--.

Column 4, line 2 "7?C." should be --7°C.--.

Column 4, line 18, "psycrotrophic" should be --psychrotrophic--.

Column 4, line 68 (Claim 1) "Lactobacilis" should be --Lactobacillus--.

Column 5, line 5, (Claim 1) "80°C" should be --8°C--.

Column 5, line 6, (Claim 1) after "milk", --and-- should be inserted.

Column 6, line 4, (Claim 4) "2-2, azinobis" should be --2,2' azinobis--.

Signed and Sealed this

Twenty-first Day of May, 1991

*Attest:*

HARRY F. MANBECK, JR.

*Attesting Officer*  *Commissioner of Patents and Trademarks*